(12) United States Patent
Ries et al.

(10) Patent No.: US 8,574,306 B2
(45) Date of Patent: Nov. 5, 2013

(54) ACETABULAR CUP

(75) Inventors: Michael D. Ries, Tiburon, CA (US); Karen E. Mohr, Salt Lake City, UT (US)

(73) Assignee: Michael D. Ries, Tiburon, CA (US)

( * ) Notice: Subject to any disclaimer, the term of this patent is extended or adjusted under 35 U.S.C. 154(b) by 0 days.

(21) Appl. No.: 13/399,173

(22) Filed: Feb. 17, 2012

(65) Prior Publication Data

US 2012/0158154 A1 Jun. 21, 2012

Related U.S. Application Data

(62) Division of application No. 12/478,260, filed on Jun. 4, 2009, now Pat. No. 8,211,184.

(60) Provisional application No. 61/170,735, filed on Apr. 20, 2009, provisional application No. 61/171,984, filed on Apr. 23, 2009.

(51) Int. Cl.
*A61F 2/32* (2006.01)

(52) U.S. Cl.
USPC ............... 623/22.21; 623/22.22; 623/22.35; 623/22.36

(58) Field of Classification Search
CPC .................................. A61F 2/36; A61F 2/34
USPC ................................ 623/22.11, 22.21–22.39
See application file for complete search history.

(56) References Cited

U.S. PATENT DOCUMENTS

| | | |
|---|---|---|
| 4,795,470 A | 1/1989 | Goymann et al. |
| 4,840,632 A | 6/1989 | Kampner |
| 4,955,919 A | 9/1990 | Pappas et al. |
| 5,108,445 A | 4/1992 | Ashby |
| 5,133,764 A | 7/1992 | Pappas et al. |
| 5,176,711 A | 1/1993 | Grimes |
| 5,192,329 A | 3/1993 | Christie et al. |

(Continued)

FOREIGN PATENT DOCUMENTS

| | | |
|---|---|---|
| EP | 0303006 A1 | 2/1989 |
| EP | 00472315 A1 | 2/1992 |
| EP | 01588677 A2 | 10/2005 |
| EP | 01681036 A1 | 7/2006 |

OTHER PUBLICATIONS

International Search Report for PCT/US2010/030041 dated Jan. 25, 2011.

(Continued)

*Primary Examiner* — Jason-Dennis Stewart
(74) *Attorney, Agent, or Firm* — Lerner, David, Littenberg, Krumholz & Mentlik, LLP

(57) ABSTRACT

A method for placing a prosthetic acetabular cup within an acetabulum comprises implanting an acetabular cup with an eccentric socket. The acetabular cup may be substantially hemispherical with a cup rim and a portion of the cup rim removed defining a relief. The cup may accommodate a concentric liner in an eccentric position. Screw apertures may be present on the periphery of the cup and the screw trajectories may converge toward the dome of the cup. The cup is attached to a tool which is offset relative to the cup because of the substantially eccentric socket. The relief, when the cup is secured to the acetabulum, is positioned substantially anterior and the socket is positioned more posterior to provide a more natural center of rotation of a femoral head within the socket. The first relief reduces impingement of the acetabular cup on soft tissue.

14 Claims, 12 Drawing Sheets

(56) References Cited

U.S. PATENT DOCUMENTS

| | | |
|---|---|---|
| 5,326,368 A | 7/1994 | Collazo |
| 5,370,704 A | 12/1994 | DeCarlo, Jr. |
| 5,376,122 A | 12/1994 | Pappas et al. |
| 5,458,650 A | 10/1995 | Carret et al. |
| 5,507,825 A | 4/1996 | Frei |
| 5,824,107 A | 10/1998 | Tschirren |
| 5,879,399 A | 3/1999 | Church |
| 5,928,288 A | 7/1999 | Wilson |
| 5,931,870 A | 8/1999 | Cuckler et al. |
| 6,136,034 A | 10/2000 | Townley |
| 6,290,727 B1 | 9/2001 | Otto et al. |
| 6,520,995 B2 | 2/2003 | Church |
| 6,620,200 B1 | 9/2003 | Descamps et al. |
| 6,896,703 B2 | 5/2005 | Barbieri et al. |
| 7,022,142 B2 | 4/2006 | Johnson |
| 7,169,185 B2 | 1/2007 | Sidebotham |
| 7,604,667 B2 | 10/2009 | DeSmet et al. |
| 7,833,276 B2 | 11/2010 | Auxepaules et al. |
| 2003/0153982 A1 | 8/2003 | Pria |
| 2006/0167556 A1* | 7/2006 | Lazennec et al. .......... 623/22.24 |
| 2008/0021568 A1 | 1/2008 | Tulkis et al. |
| 2008/0262627 A1* | 10/2008 | DeSmet et al. ............ 623/22.36 |

OTHER PUBLICATIONS

Wright Medical Technology, Inc., Conserve Total, A-Class Advanced Metal, 2005.
Wright Medical Technology, Inc., Conserve Total, Super-Fix Acetabular System, 2005.
Australian Examination Report for Application No. 2010239614 dated Aug. 1, 2013.

* cited by examiner

ACETABULAR CUP

CROSS-REFERENCE TO RELATED APPLICATIONS

The present application is a divisional of U.S. patent application Ser. No. 12/478,260, filed Jun. 4, 2009, which claims the benefit of the filing date of U.S. Provisional Patent Application No. 61/170,735 filed Apr. 20, 2009 and U.S. Provisional Patent Application No. 61/171,984 filed Apr. 23, 2009, the disclosures of which are hereby incorporated herein by reference.

BACKGROUND OF THE INVENTION

1. The Field of the Invention

The present invention relates generally to an acetabular cup implanted in a natural acetabulum and more particularly, the eccentric position of a socket within the acetabular cup and bevel of the anterior rim for use with a prosthetic femoral head to provide a more natural anatomic placement and function.

2. The Relevant Technology

When a primary total hip arthroplasty fails and requires surgical treatment with revision total hip arthoplasty, the previously implanted acetabular component is removed and a new acetabular cup implanted. Bone loss surrounding the acetabular component may also be present so that the revision acetabular cup is larger than the previously implanted primary acetabular cup. The revision (or jumbo) cup is therefore larger than the normal anatomic size of the acetabulum. Currently jumbo acetabular cups are used for acetabular cup revisions as well as for primary arthroplasty in patients with peri-acetabular bone defects, such as congenital hip dysplasia. Jumbo cups provide a large surface area for fixation to the bone and have better long term implant stability when using cementless fixation rather than cemented fixation. These jumbo cups restore the center of rotation of the hip more toward its anatomical location as compared to smaller cups that are placed into a superior bone defect above the anatomic acetabulum. Although current jumbo cups tend to have the socket of the cup centered within the metal shell, the cup is larger than the anatomic acetabulum which still causes the center of rotation of the hip joint to be higher than is ideal biomechanically.

Since current jumbo cups are larger than the anatomic dimensions of the native acetabulum, a portion of the rim of the cup often protrudes from the bone. This protrusion can cause impingement and irritation with the surrounding soft tissue such as the iliopsoas tendon, causing groin pain. This soft tissue impingement occurs most often on the anterior portion of the cup after being implanted into a natural acetabulum. However, soft tissue impingement can occur in more than just the anterior location.

Current jumbo cups are attached to the pelvis with screws placed through holes in the cup. Multiple screw holes are usually provided to permit variable placement of screws into the remaining peri-acetabular bone. Jumbo cups typically have screw holes in the peripheral portion of the cup which are inserted perpendicular to the face or rim of the cup. However, since the cup is larger than the normal acetabulum, the peripheral screws may be directed peripheral to the remaining peri-acetabular bone stock.

There is a need to have an acetabular cup that can provide a more natural anatomical center of rotation while allowing for greater fixation in the acetabulum. The cup should have the ability to use multiple cup liners or none at all. The cup should also reduce impingement on surrounding soft tissue.

As the above described techniques illustrate, the existing systems and procedures for acetabular cups may not be as effective as desired.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION

The present invention relates to systems and methods for acetabular cups; for securing a cup into a natural acetabulum and providing a more natural center of rotation and a more natural anatomic fit with a natural or prosthetic femoral head. Those of skill in the art will recognize that the following description is merely illustrative of the principles of the invention, which may be applied in various ways to provide many different alternative embodiments. This description is made for the purpose of illustrating the general principles of this invention and is not meant to limit the inventive concepts in the appended claims.

One embodiment of the present invention includes an acetabular cup with a first relief on first end of the cup, an eccentric socket within the cup and a plurality of apertures to allow for passage of a plurality of screws. The cup further comprises an outer wall with a first geometric center and a socket with a second geometric center separate from the first geometric center configured to receive a natural or prosthetic femoral head. The eccentric socket provides a center of rotation for the femoral head in a more natural anatomic location. The cup further comprises a cup rim between the socket and the outer wall with a first relief and multiple apertures around the cup rim. The socket may be configured to receive a liner with a bearing surface to contact the femoral head. The socket may also provide a bearing surface configured to interact with the femoral head without a liner. The cup is positioned within a natural acetabulum or host bone and the socket provides securement of the femoral head while the first relief reduces impingement of the acetabular cup on soft tissue. The first relief reduces soft tissue impingement without decreasing the contact surface area of the cup for fixation with the host bone. With the combination of the eccentric location of the liner socket, the first relief does not reduce the contact area between the cup and liner or the liner and the femoral head.

The following definition should be used with regard to this application: a "relief" means a portion of an acetabular cup or hemispherical cup that has been removed to reduce impingement of the cup on soft tissue.

Figure 1:
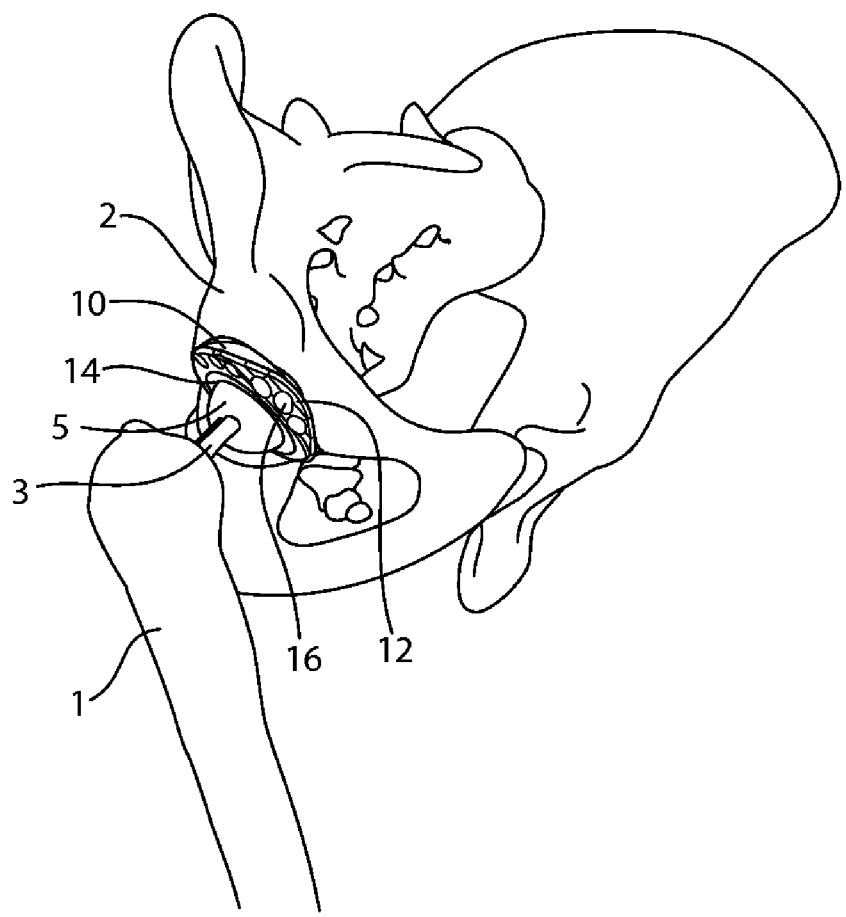
FIG. 1 illustrates an anterior side view of a complete hip assembly, with a pelvic bone, femur, femoral head prosthetic and an acetabular cup.
Figure 2:
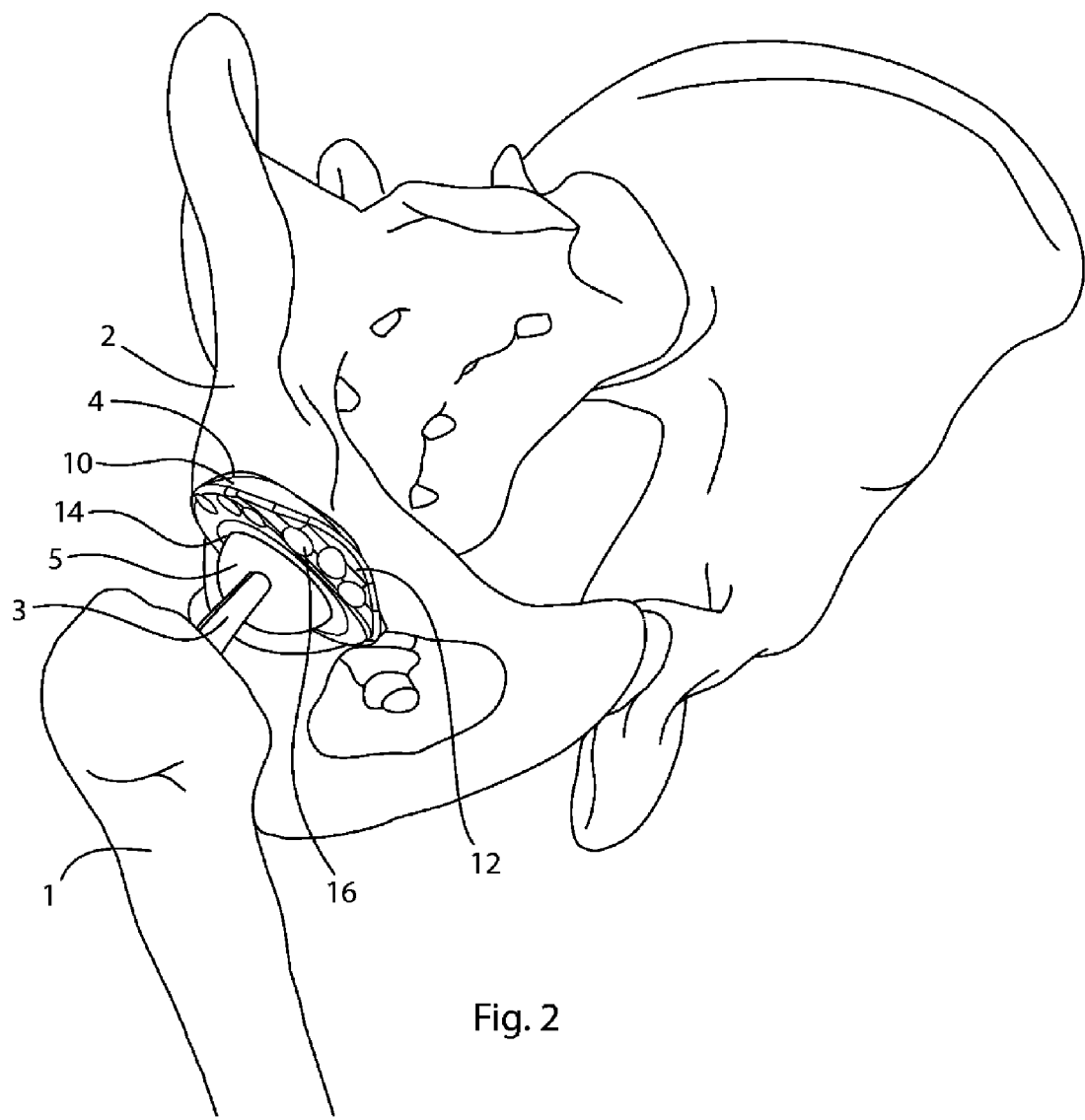
FIG. 2 illustrates an enlarged anterior side view of the complete hip assembly of FIG. 1.

Referring to FIGS. 1 and 2, an acetabular cup 10, which may be substantially hemispherical or dome shaped which may allow implantation with standard hemispherical reamers, is positioned in an acetabulum 4 of a pelvic bone 2. A prosthetic femoral head 5 is position in a socket 14 of the acetabular cup 10 the femoral head 5 extends from a prosthetic hip stem 3 which has been positioned within a femur 1 of a patient. It will be appreciated that a prosthetic femoral head and hip stem are not required and a natural femur with a natural or resurfaced femoral head positioned within the acetabular cup 10 may also be used. The femoral head 5 is positioned within a socket 14 of the acetabular cup 10.

Figure 3:
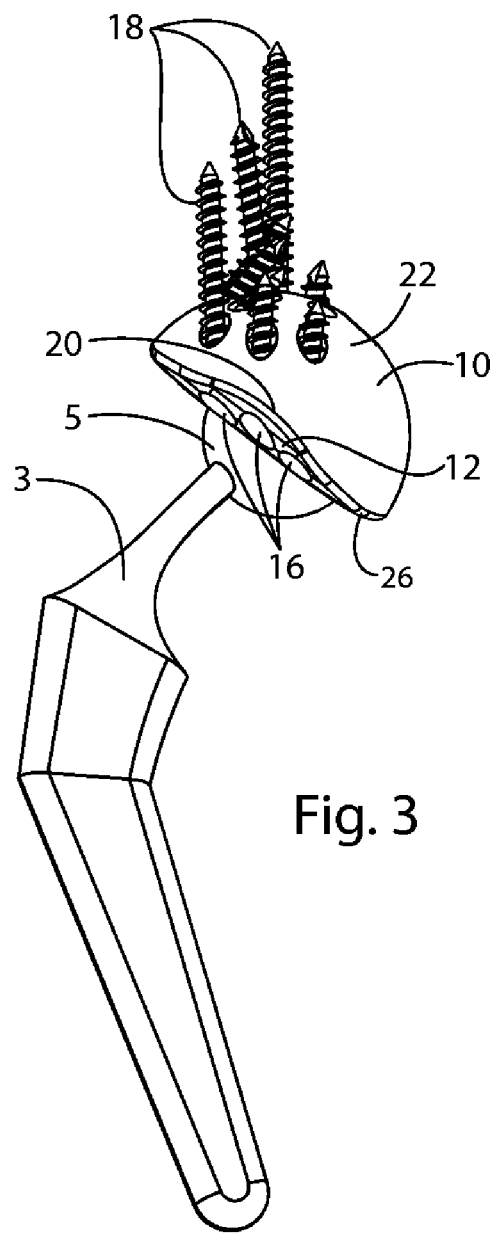
FIG. 3 illustrates a side view of the complete hip assembly of FIG. 1 without the human anatomy.

Referring to FIG. 3, the acetabular cup 10 comprises an outer wall 22 and a cup rim 26. The acetabular cup 10 outer wall 22 may include a porous coating to allow or encourage bone ingrowth. The outer wall 22 may comprise a plurality of apertures 16, 28, 30 (cup rim apertures 30 not shown) configured in a plurality of directions. In addition the outer wall 22 may comprise an inserter aperture 29 which may be larger than the plurality of apertures 28. The inserter aperture 29 may threadably receive an inserter instrument (not pictured) for inserting the acetabular cup 10 into the acetabulum 4. Each of the apertures 16, 28, 30 is configured to receive at least one screw 18. One, some, or all of the apertures 16, 28, 30 may be smooth to allow the passage of screws, nails or other fixation elements. The screw 18 may be threaded and may include a locking screw that locks into the cup 10, a bone screw or a morse/taper screw. The screw 18 may also include a nail or other devices known in the art may be used to pass through the apertures 16, 28, 30 to further secure the acetabular cup 10 to the acetabulum 4. A plurality of screws 18 may be used to secure the acetabular cup 10 to the acetabulum 4. The screws may be completely embedded in the pelvic bone.

Alternate embodiments of securement of the acetabular cup 10 to the inserter instrument may include more than one aperture configured to connect to the inserter. In addition the inserter instrument aperture(s) 29 may be smooth and alternate mechanism for fixation of the inserter to the acetabular cup may include snap fit, press fit, collet, or bayonet fixation.

Other embodiments of securement of the acetabular cup 10 to the acetabulum 4 may include press fitting the cup within the acetabulum 4, heating the cup 10 before placing the cup 10 within the acetabulum 4 allowing the cup 10 to expand as it cools within the acetabulum.

Figure 4:
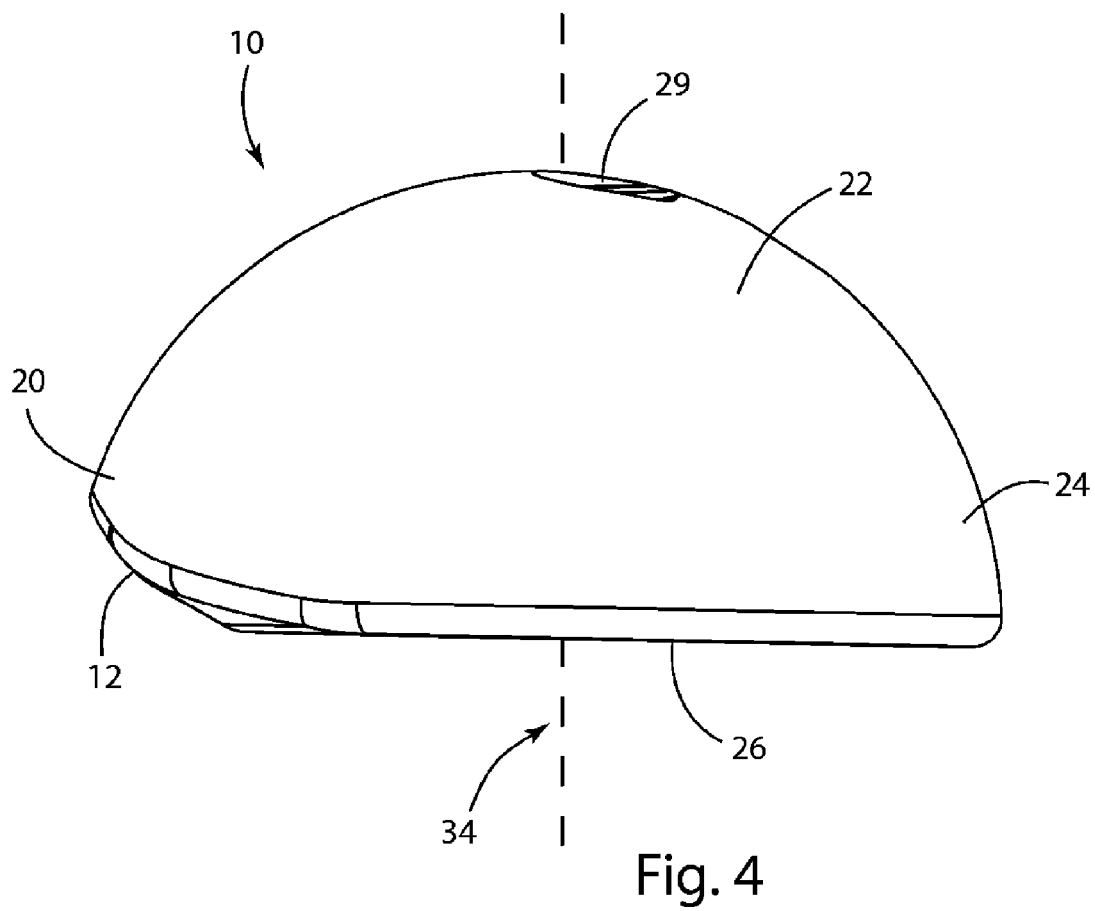
FIG. 4 illustrates a side view of the acetabular cup of FIG. 1 with a first relief on one end of the cup, a first geometric center axis of the cup and an aperture configured to receive an inserter instrument.

Referring to FIG. 4, the outer wall 22 of the acetabular cup 10 comprises a first geometric center axis 34 substantially perpendicular to the cup rim 26 as well as a first end 20 and a second end 24 located opposite the first end 20 of the cup 10. A portion of the cup rim 26 defines a first relief 12 displaced toward the first end 20.

Figure 5:
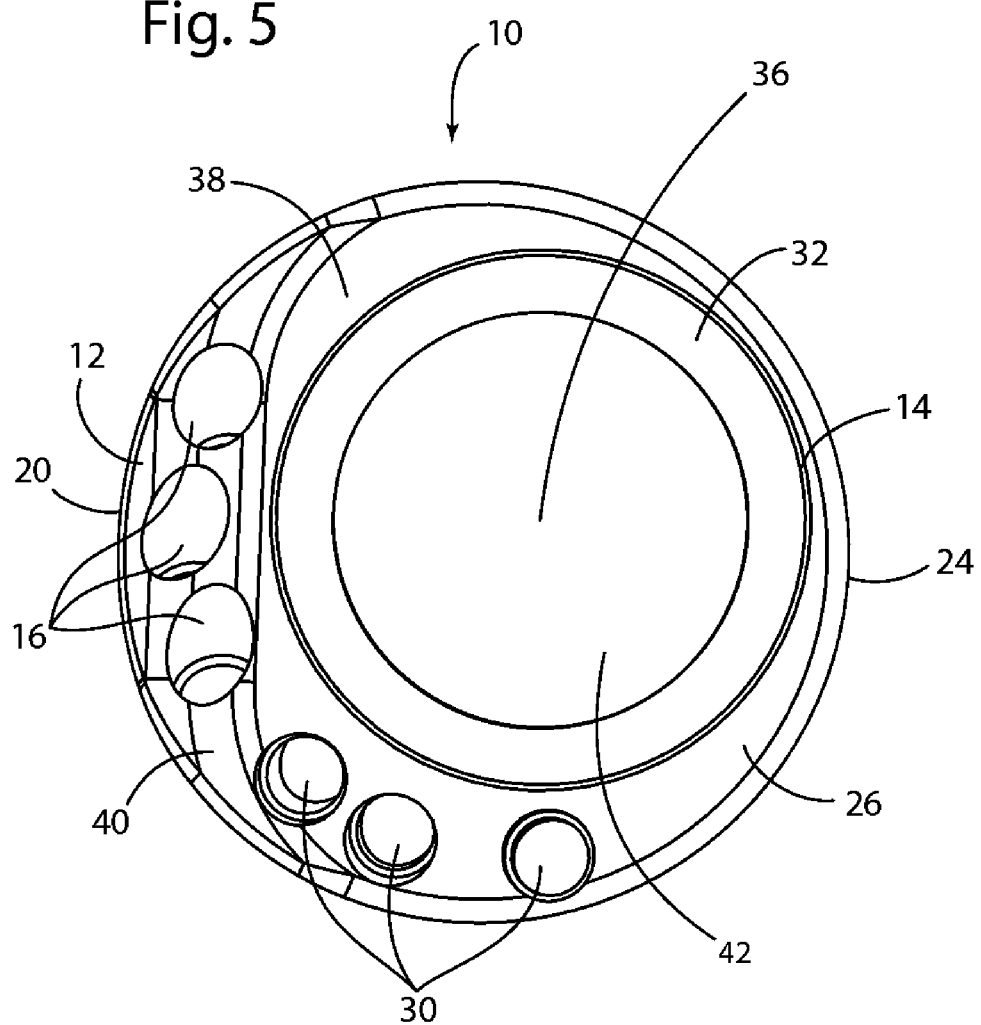
FIG. 5 illustrates a bottom view of the acetabular cup of FIG. 4 with an eccentric socket and apertures configured to receive screws.

Referring to FIG. 5, the cup rim 26 extends from the socket 14 to the outer wall 22 of the acetabular cup 10. The socket 14 may have the ability to accommodate a cup liner 32 with a liner bearing surface 42 to interact with the femoral head 5. The shape of the acetabular cup 10 and socket 14 may allow a plethora of standard cup liners 32 to be used, including, but not limited to constrained liners, unconstrained liners, and liners made from a variety of materials including, but not limited to ultra high molecular weight polyethylene, other polymer bearing materials, metal bearing materials, or ceramic bearing materials. The socket 14 may also comprise a socket bearing surface 44 to interact with the femoral head 5 without a cup liner 32.

The cup rim 26 may comprise two surfaces a first surface 38 and a second surface 40. The first surface of the cup rim extends from the socket 14 to the outer wall 22 in a first plane. The second surface extends from the socket 14 to the outer wall 22 in a second plane which is non-parallel with the first plane. The cup rim may also comprise a plurality of rim apertures 30 configured to receive screws 18. The cup rim apertures 30 may be substantially perpendicular to the cup rim 26. The cup rim apertures 30 may extend parallel, non-parallel or skew to the first geometric center axis 34. The cup rim apertures 30 may be smooth to allow for passage of the screw 18 or threaded to threadably receive the screw. Alternate fixation devices may be used including a nail or other devices known in the art for securing prosthesis to bone.

The first relief 12 may also comprise first relief apertures 16 which may be perpendicular to the first relief 12. The first relief apertures 16 may extend substantially toward the first geometric center axis 34, away from the first geometric center axis 34 or skew from the first geometric center axis 34. The first relief apertures 16 may also be threaded or smooth as set forth previously herein.

Figure 6:
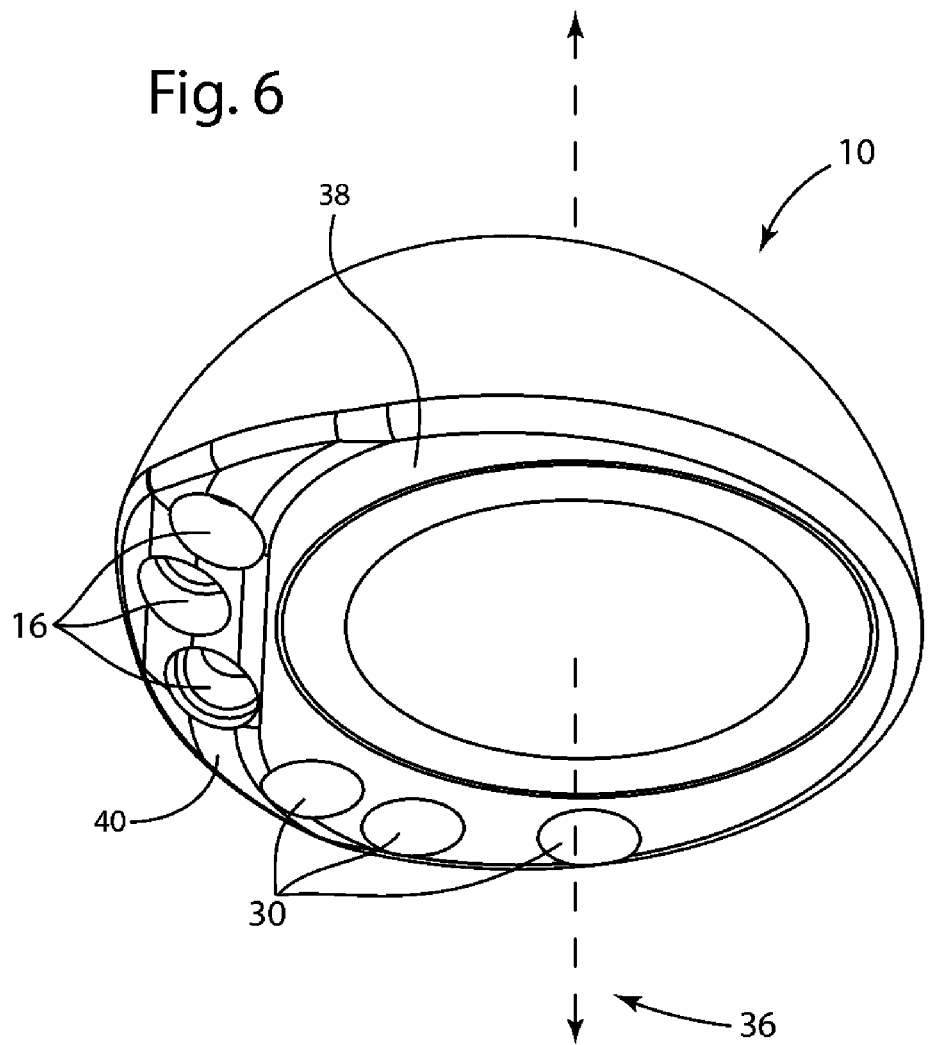
FIG. 6 illustrates a bottom perspective view of the acetabular cup of FIG. 4 with a socket, socket liner and a second geometric center axis of the socket.

Referring to FIG. 6, the socket comprises a second geometric center axis 36 which may be substantially parallel to the first geometric center axis 34. The second geometric center axis 36 is displaced from the first geometric center axis 34 defining a substantially eccentric socket 14 within the acetabular cup 10. The eccentric socket 14 is displaced closer to the second end 24 of the cup 10 and further displaced from the first end 20. The position of the socket 14 creates a center of rotation of the either natural or prosthetic femoral head 5 toward a natural anatomic location after implantation of the acetabular cup in an acetabulum 4 and after placement of the femoral head 5 in the socket 14.

Even though the socket 14 is eccentric the socket 14 may maintain a standard concentric cup liner 32 as stated previously herein. In addition even with a removal of a portion of the cup rim, the first relief 12, the contact area between the cup 10 and the liner 32 or between the liner 32 and the femoral head 5 is not reduced. The combination of features allows the femoral head 5 to be fully constrained in the anatomic position. However, the acetabular cup 10 may include further constraint of the femoral head 5 by using a modular rim component (not shown).

Figure 7:
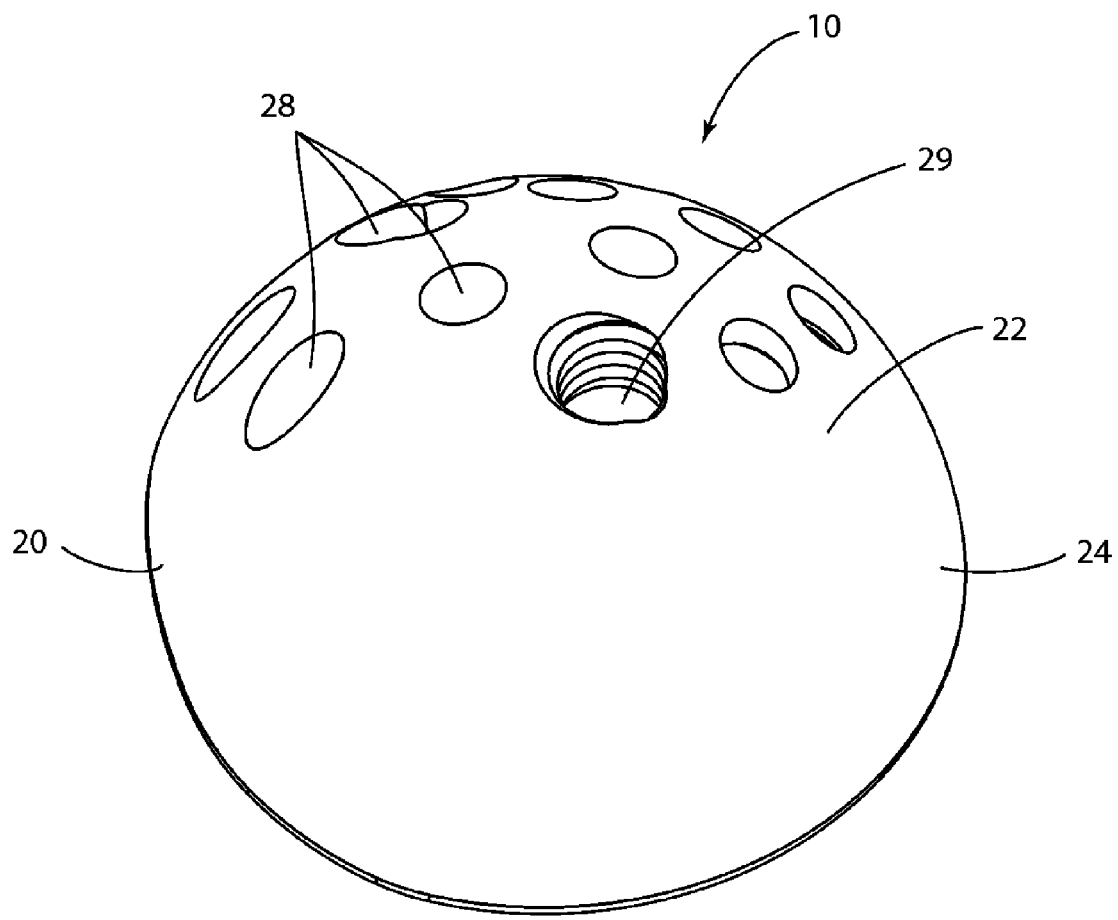
FIG. 7 illustrates a top perspective view of the acetabular cup of FIG. 4 with a plurality of apertures configured to receive screws and the inserter instrument aperture.
Figure 8:
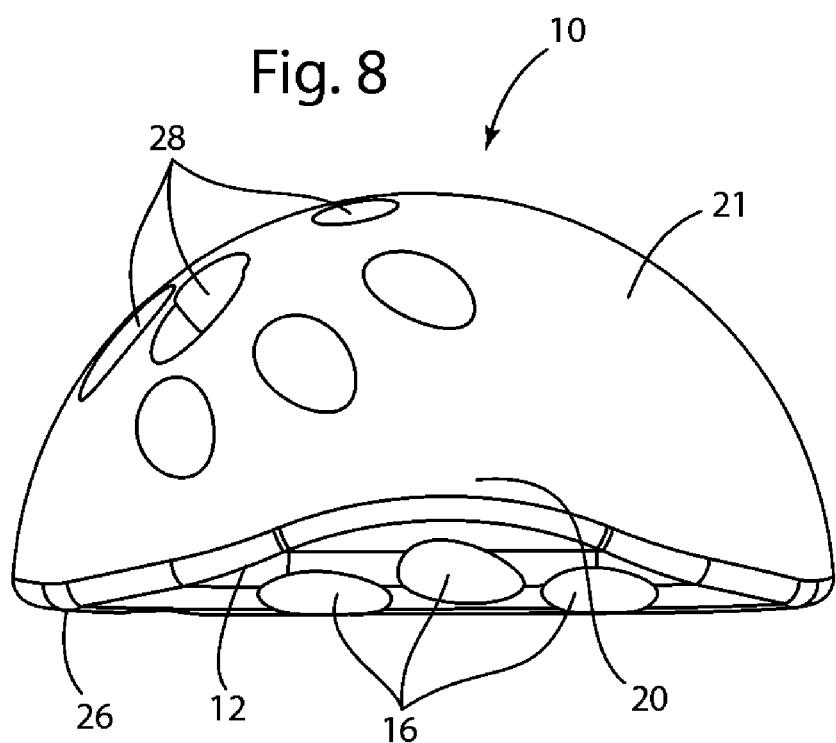
FIG. 8 illustrates an alternate side view of the acetabular cup of FIG. 4 with a plurality of apertures and a first relief on one end of the cup.

Referring to FIGS. 7 and 8, the plurality of apertures 16, 28, 30 is displaced about the outer wall 22 with varying distances between each other and the cup rim 26. The apertures 16, 28, 30 may vary in size as may the screw's 18 (not shown) size.

Figure 9:
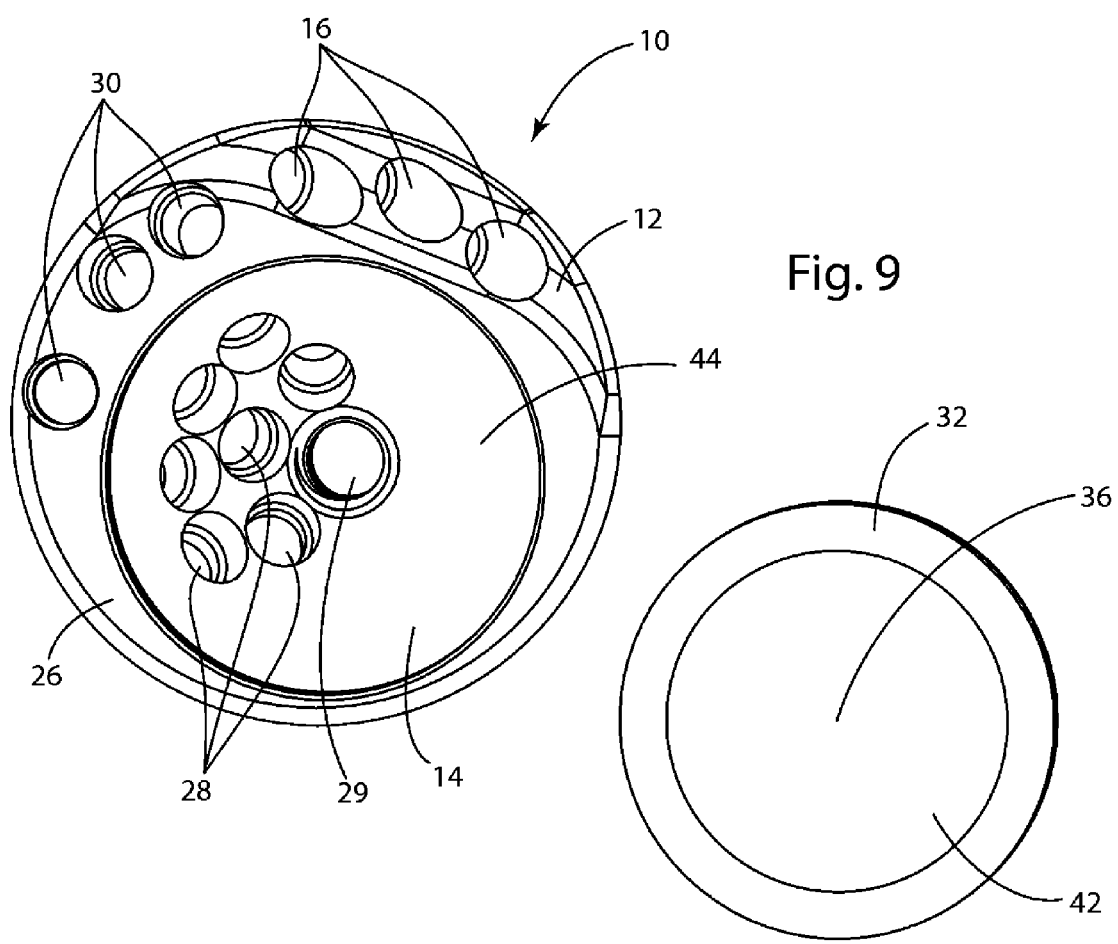
FIG. 9 illustrates a bottom perspective view of the acetabular cup of FIG. 6 with the cup liner removed from the socket.

Referring to FIG. 9, the cup liner 26 is removed from the socket to show the socket bearing surface 44 which may interact either with a cup liner 32 or the femoral head 5. The plurality of apertures 16, 28, 30 are shown with socket apertures 30 positioned within the socket 14 at varying distances from each other and from the cup rim 26. The socket apertures may be threaded in the case of screw 18 fixation or may be smooth in the case of an alternate form of fixation, for example a nail.

Figure 10:
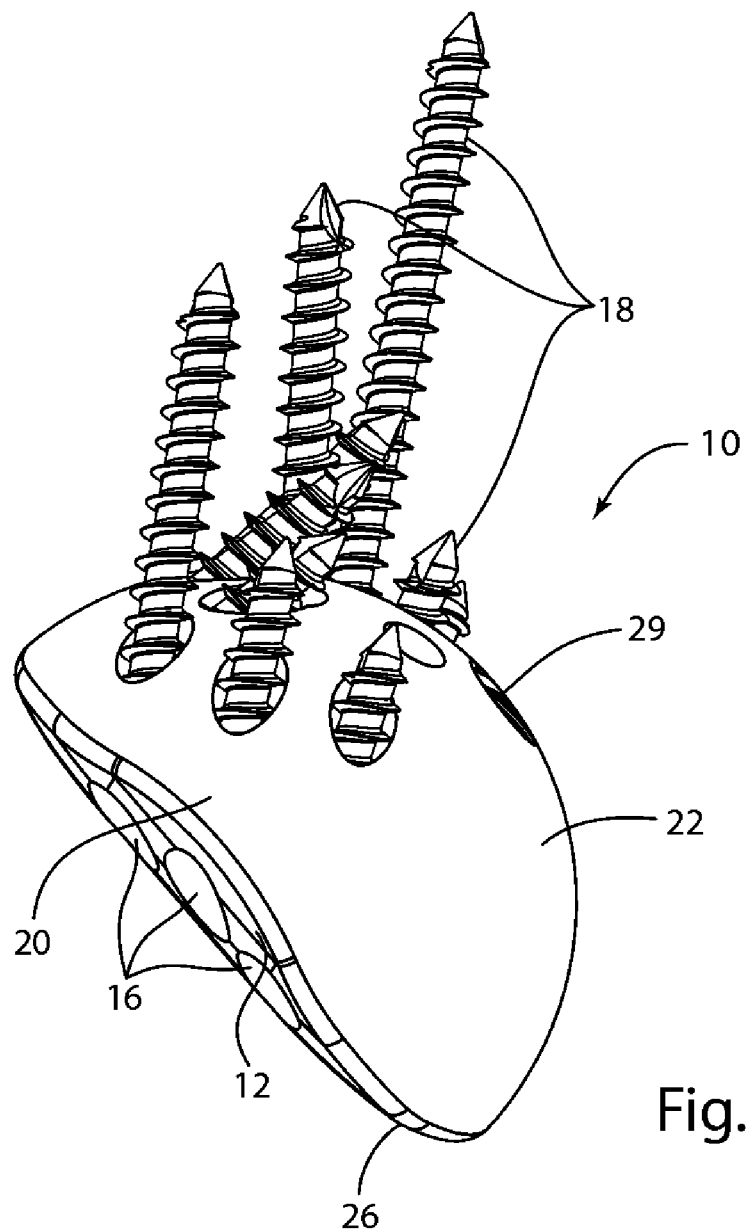
FIG. 10 illustrates an alternate side view of the acetabular cup of FIG. 4 substantially as it would be positioned in an acetabulum showing a first relief and a plurality of apertures.

Referring to FIG. 10, the illustration depicts the acetabular cup 10 positioned substantially as it would be within the acetabulum 4. Referring back to FIGS. 1 and 2 as well, the first relief 12 is positioned substantially anterior within a patient and substantially anterior to the socket 14 of the cup 10. The plurality of apertures 16, 28, 30 are positioned to point in various directions including parallel to the first geometric center axis 34, pointing toward the axis of the first geometric center 34, or point away from the axis of the first geometric center 34, to provide adequate fixation of the cup 10 to the acetabulum 4.

Figure 11:
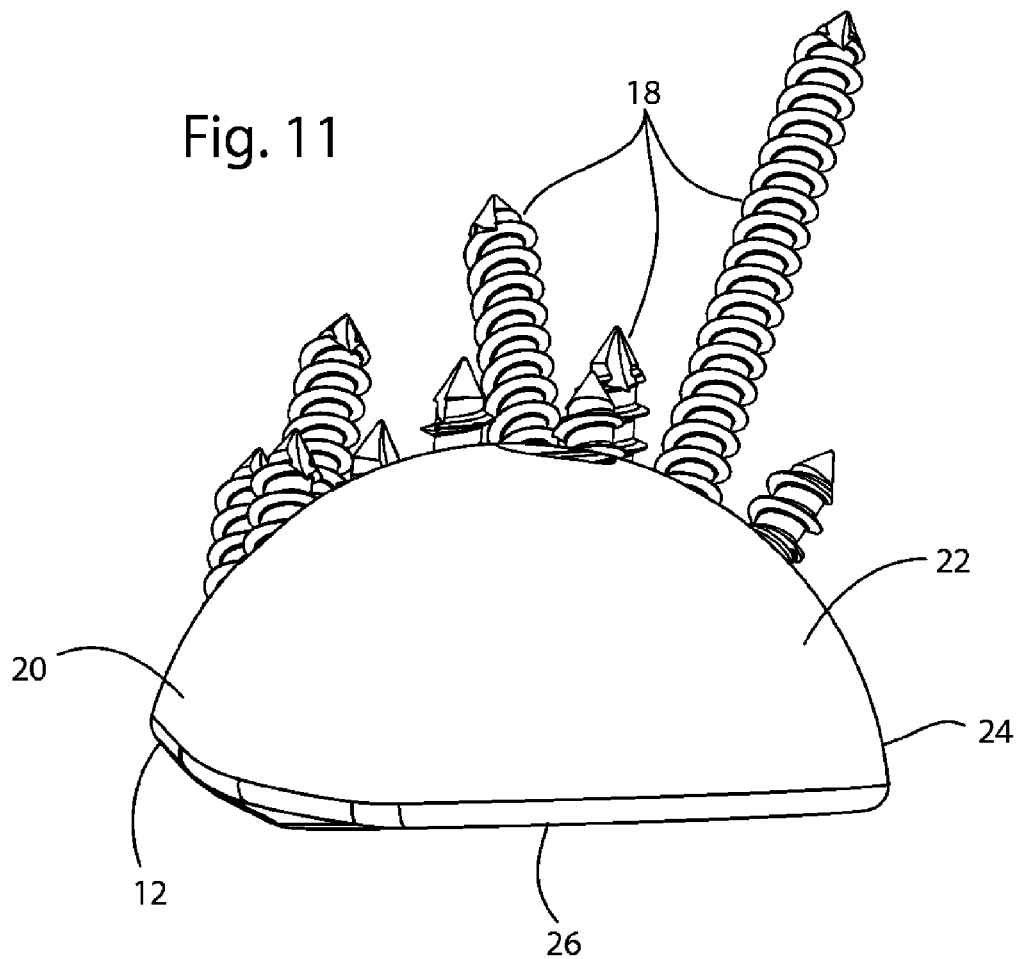
FIG. 11 illustrates a side view of the acetabular cup of FIG. 4 with a plurality of screws passing through the plurality of apertures.
Figure 12:
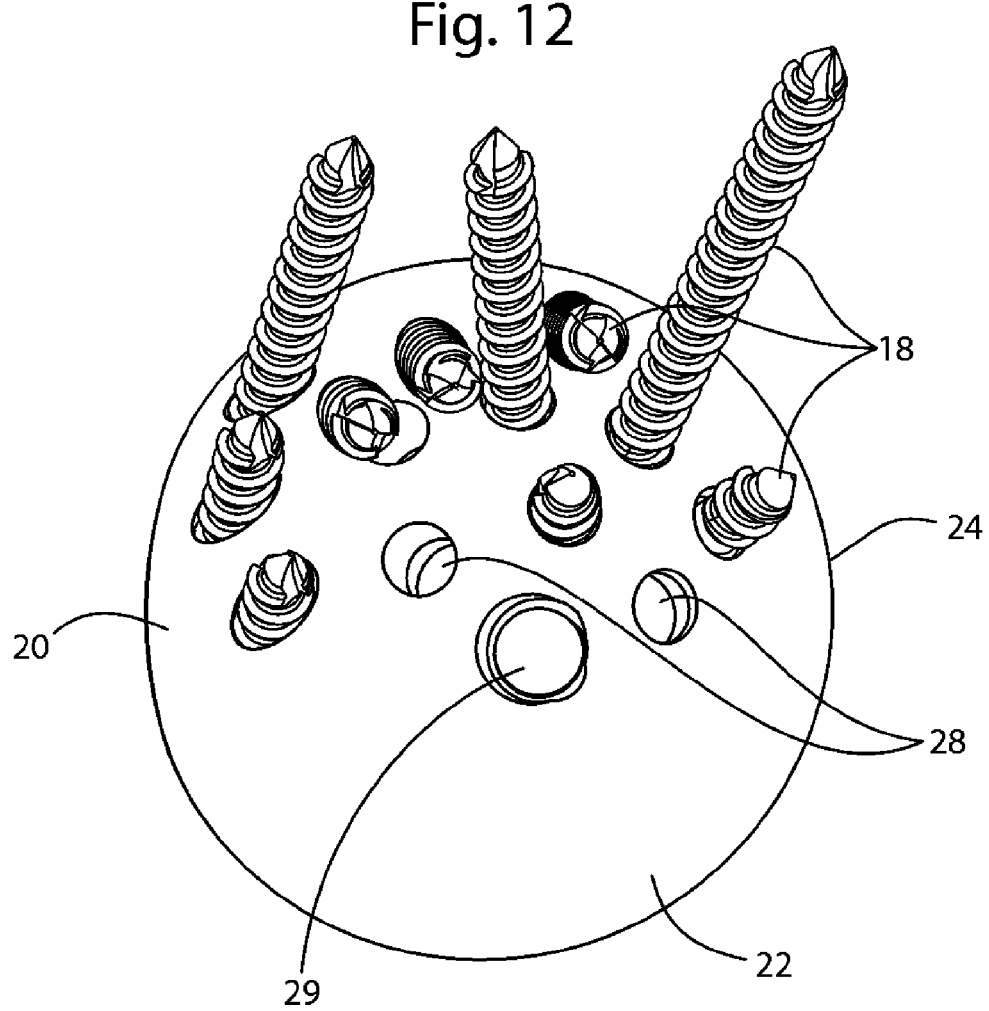
FIG. 12 illustrates a top view of the acetabular cup of FIG. 12 with the plurality of screws passing through some of the plurality of apertures.

Referring to FIGS. 11 and 12, the trajectory of the screws 18 is demonstrated in various directions. Some of the screws 18 may be directed toward the first geometric center axis 34 whereas other screws 18 are directed parallel with the first geometric center axis 34 or directed away from first geometric center axis 34.

The acetabular cup 10 may be comprised of many different materials including titanium, cobalt chrome, stainless steel, ceramic or other biocompatible material. The outer coating of the cup 10 may be porous and may be comprised of titanium, cobalt chrome, polymer or other biocompatible material. In addition the cup 10 may be a combination of different biocompatible materials. For example, the cup 10 may be cobalt chrome with a titanium porous coating on the outer wall 22.

The method for inserting the acetabular cup 10 into the acetabulum 4 may include attaching an inserter (not shown) to the acetabular cup within the socket 14. The inserter is offset from the first geometric center axis 34, offset relative to the outer wall 22 of the acetabular cup 10, because the inserter is attached to the offset or eccentric socket 14. The cup may then be inserted into the acetabular space of the acetabulum and positioned such that the socket 14 center is placed toward a natural anatomic location and the first geometric center axis 34 of the outer wall 22 of the acetabular cup 10 is positioned superior the second geometric center axis 36. The acetabular cup 10 may then be secured to the acetabulum by any method previously described or any other method known in the art. The inserter may then be detached from the acetabular cup 10.

The same method previously described may be used, in reverse, when removing the acetabular cup 10 in case of revisionary procedures. The inserter may be attached to the acetabular cup 10 offset from the first geometric center axis. The screws or other securement mechanism would then be removed from the acetabular cup 10 and then the acetabular cup 10 removed from the acetabulum 4.

An alternate embodiment of the acetabular cup 10 may include the relief 12 being positioned, within the acetabulum 4, either substantially superior, substantially inferior or substantially posterior. Furthermore the acetabular cup may include more than one relief. Such multiple reliefs may intersect along the cup rim 26 or may have a portion of the cup rim 26 between each of the reliefs.

Other alternate embodiments may include a beveled cup rim with tangents extending away from the center of the geometric center of the acetabular cup or the geometric center of the socket. The cup rim may include a symmetric or non-symmetric bevel on opposite ends of the acetabular cup essentially removing portions of the cup rim. The cup rim may also have a single bevel on one end of the cup which may be on one face of the cup opposite the cup liner. Alternatively the cup rim may have a bevel added on top of the cup rim.

The present invention may be embodied in other specific forms without departing from its spirit or essential characteristics. For example, above are described various alternative examples of acetabular cups. It is appreciated that various features of the above-described examples can be mixed and matched to form a variety of other combinations and alternatives. It is also appreciated that this system should not be limited to simply to acetabular cups and hip joint replacement. This system may also be used to replace a shoulder joint or other substantially similar joints. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for replacing a hip joint, the method comprising:
   inserting an acetabular cup into a natural acetabulum, the acetabular cup comprising:
   a substantially hemispherical outer wall defining a first geometric center;
   a substantially hemispherical socket defining a second geometric center displaced from the first geometric center;
   a cup rim extending between the substantially hemispherical outer wall and the substantially hemispherical socket, the cup rim defining a first relief;
   securing the acetabular cup into the natural acetabulum; and
   positioning a natural or prosthetic femoral head in the socket such that the natural or prosthetic femoral head is rotatable about the second geometric center to approximate natural hip motion; and
   wherein inserting the acetabular cup into the natural acetabulum comprises positioning the first relief substantially anteriorly when inserted into the natural acetabulum.

2. A method for replacing a hip joint, the method comprising:
   inserting an acetabular cup into a natural acetabulum, the acetabular cup comprising:
   a substantially hemispherical outer wall defining a first geometric center; and
   a substantially hemispherical socket defining a second geometric center displaced from the first geometric center;
   a cup rim extending between the substantially hemispherical outer wall and the substantially hemispherical socket, the cup rim defining a first relief;
   securing the acetabular cup into the natural acetabulum; and
   positioning a natural or prosthetic femoral head in the socket such that the natural or prosthetic femoral head is rotatable about the second geometric center to approximate natural hip motion, wherein inserting the acetabular cup into the natural acetabulum comprises positioning the first relief substantially posteriorly when inserted into the natural acetabulum.

3. A method for replacing a hip joint, the method comprising:
   inserting an acetabular cup into a natural acetabulum, the acetabular cup comprising:
   a substantially hemispherical outer wall defining a first geometric center; and
   a substantially hemispherical socket defining a second geometric center displaced from the first geometric center;
   a cup rim extending between the substantially hemispherical outer wall and the substantially hemispherical socket, the cup rim defining a first relief;
   securing the acetabular cup into the natural acetabulum; and
   positioning a natural or prosthetic femoral head in the socket such that the natural or prosthetic femoral head is rotatable about the second geometric center to approximate natural hip motion, wherein inserting the acetabular cup into the natural acetabulum comprises positioning the first relief substantially superiorly when inserted into the natural acetabulum.

4. A method for replacing a hip joint, the method comprising:
   inserting an acetabular cup into a natural acetabulum, the acetabular cup comprising:
   a substantially hemispherical outer wall defining a first geometric center; and
   a substantially hemispherical socket defining a second geometric center displaced from the first geometric center;
   a cup rim extending between the substantially hemispherical outer wall and the substantially hemispherical socket, the cup rim defining a first relief;
   securing the acetabular cup into the natural acetabulum; and
   positioning a natural or prosthetic femoral head in the socket such that the natural or prosthetic femoral head is rotatable about the second geometric center to approximate natural hip motion, wherein inserting the acetabular cup into the natural acetabulum comprises positioning the first relief substantially inferiorly when inserted into the natural acetabulum.

5. A method for replacing a hip joint, the method comprising:
   inserting an acetabular cup into a natural acetabulum, the acetabular cup comprising:
   a substantially hemispherical outer wall defining a first geometric center;
   a substantially hemispherical socket defining a second geometric center displaced from the first geometric center;
   a cup rim extending between the substantially hemispherical outer wall and the substantially hemispherical socket, the cup rim defining a first relief;
   securing the acetabular cup into the natural acetabulum;
   positioning a natural or prosthetic femoral head in the socket such that the natural or prosthetic femoral head is rotatable about the second geometric center to approximate natural hip motion;
   securing the acetabular cup into the natural acetabulum using a plurality of screws passing through a plurality of apertures sized and shaped to receive the plurality of screws; and
   wherein securing the acetabular cup into the natural acetabulum further comprises passing the plurality of screws through the plurality of apertures positioned on the first relief of the cup rim, wherein the apertures on the first relief are oriented non-parallel to an axis through the first geometric center of the outer wall perpendicular to a plane through the rim.

6. The method as set forth in claim 5 inserting at least one of the screws in a non-parallel direction with respect to the first geometric center axis.

7. The method as set forth in claim 5 inserting at least one of the screws a direction towards the first geometric center axis, inserting at least one screw in a direction away from the first geometric center axis and inserting at least one screw in a direction parallel to the first geometric center axis.

8. A method for replacing a hip joint comprising:
   inserting an acetabular cup into an acetabulum, the acetabular cup having a substantially hemispherical outer surface sized and shaped for implantation in the acetabulum, the substantially hemispherical outer surface having a first axis through a center of the outer surface perpendicular to a plane through a cup rim, the acetabular cup further comprising a socket having a part-spherical inner surface, the part spherical inner surface having an opening for receiving a natural or prosthetic femoral head, the socket having a second axis through a center of the part-spherical inner surface, the first and second axis being parallel, the second axis being offset from the first axis in a first direction, the acetabular cup rim surface extends outwardly in a second direction different than the first direction from a portion of a circumference of the opening of the socket inner surface towards the substantially hemispherical outer surface, the rim surface extending outwardly at a non 90° angle to the parallel first and second axis, a plurality of non-parallel apertures extending through both the rim surface and the substantially hemispherical outer surface, the socket and the rim surface located entirely within the substantially hemispherical outer surface;
   securing the acetabular cup into the natural acetabulum; and
   positioning a natural or prosthetic femoral head in the socket such that the natural or prosthetic femoral head is rotatable about the second geometric center to approximate natural hip motion.

9. The method of claim 8, further comprising advancing a first screw through a first aperture of the cup rim wherein the cup rim further defines a first relief non-parallel to at least one aperture.

10. The method of claim 9, wherein advancing the first screw through the first aperture further comprises advancing a second screw through a second aperture positioned on the cup rim wherein the second aperture is non-parallel to the cup rim and radially spaced from the geometric center of the outer wall.

11. The method of claim 9, wherein advancing the first screw through the first aperture further comprises advancing a second screw through a second aperture positioned on the cup rim wherein the second aperture is oriented non-parallel to the first geometric center axis of the outer wall.

12. The method of claim 8, further comprising securing the acetabular cup by advancing a plurality of screws through a plurality of apertures positioned within the socket.

13. The method as set forth in claim 12 inserting at least one of the screws in a non-parallel direction with respect to the first geometric center axis.

14. The method as set forth in claim 12 inserting at least one of the screws a direction towards the first geometric center axis, inserting at least one screw in a direction away from the first geometric center axis and inserting at least one screw in a direction parallel to the first geometric center axis.

* * * * *